US010866227B2

(12) United States Patent
Rudahl et al.

(10) Patent No.: US 10,866,227 B2
(45) Date of Patent: Dec. 15, 2020

(54) EARLY WARNING SYSTEM FOR ROAD, RUNWAY, AND RAILWAY FAILURES

(71) Applicants: Kurt Rudahl, Bangkok (TH); Sally Goldin, Bangkok (TH)

(72) Inventors: Kurt Rudahl, Bangkok (TH); Sally Goldin, Bangkok (TH)

(73) Assignee: GOLDIN-RUDAHL SYSTEMS, INC., Amherst, MA (US)

( * ) Notice: Subject to any disclaimer, the term of this patent is extended or adjusted under 35 U.S.C. 154(b) by 0 days.

(21) Appl. No.: 14/467,069

(22) Filed: Aug. 25, 2014

(65) Prior Publication Data

US 2015/0219576 A1  Aug. 6, 2015

Related U.S. Application Data

(60) Provisional application No. 61/934,853, filed on Feb. 3, 2014.

(51) Int. Cl.
*G01N 33/24* (2006.01)
*G01N 33/42* (2006.01)

(52) U.S. Cl.
CPC ............. *G01N 33/24* (2013.01); *G01N 33/42* (2013.01)

(58) Field of Classification Search
CPC ...... G01N 27/025; G01G 1/042; H04Q 1/138; H04Q 2209/47
See application file for complete search history.

(56) References Cited

U.S. PATENT DOCUMENTS 4,190,776 A    2/1980  Podboronov et al.
4,795,998 A *  1/1989  Dunbar ................... G01L 1/205
                                                            338/208

(Continued)

FOREIGN PATENT DOCUMENTS

CN    202453920    9/2012
DE    19534677     4/1996

OTHER PUBLICATIONS

ASTM, Prediction of Flexible Pavement Layer Moduli from Dynaflect and FWD Deflections, American Society for Testing and Materials (ASTM) Report STP1026 [abstract only online], Jan. 1989 [retrieved on approximately Dec. 31, 2013] Retrieved from the Internet <URL: www.astm.org/DIGITAL_LIBRARY/STP/PAGES/STP19811S.htm>.

(Continued)

*Primary Examiner* — Huy Q Phan
*Assistant Examiner* — Dustin R Dickinson
(74) *Attorney, Agent, or Firm* — Danielson Legal LLC

(57) ABSTRACT

Disclosed herein is a method of detecting faults beneath a construction supported by earth. The method comprises detecting the conditions of fabric built into the construction supported by earth. One condition of the fabric indicates a fault while a second condition indicates no fault. The detected condition is associated with the location of the fabric that was built into the construction. The detected condition of the fabric is reported. Also disclosed is a fabric that can be included when constructing a road or similar construction such as a highway, railway, runway or dike. The fabric is an array of electronic circuits such that stretching or tearing said fabric will damage electrical characteristics of the fabric. An apparatus for detecting faults beneath a road is also disclosed. The apparatus comprises a fabric built into the road, and a sensor apparatus configured to measure (Continued)

conditions of the fabric at multiple locations. A subset of the conditions of the fabric indicates faults beneath the road.

16 Claims, 12 Drawing Sheets

(56) References Cited

U.S. PATENT DOCUMENTS

| | | | |
|---|---|---|---|
| 5,287,740 A | 2/1994 | Tomita | |
| 5,298,987 A | 3/1994 | Tomita | |
| 5,852,243 A | 12/1998 | Chang et al. | |
| 6,597,992 B2 | 7/2003 | Rooney | |
| 6,615,648 B1 | 9/2003 | Ferguson et al. | |
| 7,347,101 B2* | 3/2008 | Thomson | E01D 19/00 73/773 |
| 7,375,636 B1* | 5/2008 | Martin | G01R 31/2822 340/10.1 |
| 7,675,289 B1 | 3/2010 | Stolarczyk et al. | |
| 7,698,075 B2 | 4/2010 | Curry et al. | |
| 7,788,049 B2 | 8/2010 | Bryant et al. | |
| 7,925,455 B2 | 4/2011 | Pado et al. | |
| 7,950,289 B2 | 5/2011 | Foote | |
| 8,410,924 B2 | 4/2013 | Costanzo et al. | |
| 8,472,674 B2 | 6/2013 | Yevskyy et al. | |
| 8,510,048 B2 | 8/2013 | Dolgin et al. | |
| 2002/0154029 A1* | 10/2002 | Watters | G01D 5/48 340/870.07 |
| 2003/0012411 A1 | 1/2003 | Sjostrom et al. | |
| 2003/0235929 A1* | 12/2003 | Cowles | G01R 31/2884 438/17 |
| 2006/0070450 A1* | 4/2006 | Woodard | G01N 3/38 73/767 |
| 2006/0097877 A1* | 5/2006 | Baba | G06K 19/073 340/572.4 |
| 2006/0202829 A1* | 9/2006 | Girvin | G06K 19/07381 340/572.3 |
| 2007/0138304 A1* | 6/2007 | Dorfner | E01C 11/16 235/492 |
| 2007/0210966 A1* | 9/2007 | Thomas | H01Q 1/12 343/700 MS |
| 2008/0042653 A1 | 2/2008 | Bryant | |
| 2009/0020212 A1* | 1/2009 | Cacace | G01M 5/0033 156/64 |
| 2010/0067991 A9 | 3/2010 | Maggioni | |
| 2010/0073154 A1* | 3/2010 | Kim | G08G 1/042 340/435 |
| 2010/0225497 A1* | 9/2010 | Marincak | G01N 27/24 340/657 |
| 2010/0245057 A1* | 9/2010 | Chamarti | G01D 21/00 340/10.42 |
| 2011/0161008 A1 | 6/2011 | Lee | |
| 2011/0291802 A1* | 12/2011 | Fay | G01M 5/0033 340/10.1 |
| 2012/0109560 A1* | 5/2012 | Huang | G01M 5/0091 702/75 |
| 2012/0273263 A1* | 11/2012 | Nagarajan | H05K 1/097 174/257 |
| 2012/0297888 A1* | 11/2012 | Nagarajan | G01B 7/16 73/774 |
| 2013/0018585 A1 | 1/2013 | Zhdanov et al. | |
| 2013/0136539 A1 | 5/2013 | Aardema | |
| 2013/0173163 A1 | 7/2013 | Zhdanov et al. | |

OTHER PUBLICATIONS

Bonnet, Clifford F., Practical Railway Engineering, 2nd Edition, Imperial College Press, London, England, 2005. ISBN 1 86094 515 5, especially p. 86.

Cardimona, S. at al, Ground Penetrating Radar Survey of Interstate 70 Across Missouri, The University of Missouri—Rolla, Department of Geology and Geophysics and The Missouri Department of Transportation [online], pp. 5, 6, and especially 7 [retrieved on approximately Dec. 31, 2013] Retrieved from the Internet <URL: transportation.mst.edu/media/research/transportation/documents/i70.pdf>.

Daley, Margaret A. et al, Seismic Refraction Data Collected in the Chugach Mountains and along the Glenn Highway in southern Alaska in 1984, United States Department of the Interior Geologial Survey Open-File Report 85-531 [online], 1985, pp. 1 and 3, [retrieved on approximately Dec. 31, 2013] Retrieved from the Internet <URL: pubs.er.usgs.gov/publication/ofr85531>.

The U.S. Department of Transportation FHA, Ground-Penetrating Radar, Federal Highway Administration (FHA), [online] undated report FHWA-HRT-04-072,HRTS-03/01-04(1M)E [retrieved on approximately Dec. 31, 2013] Retrieved from the Internet <URL: www.fhwa.dot.gov/pavement/groundpr.pdf >.

Garber, Nicholas J. and Noel, Lester A., Traffic and Highway Engineering, 4th Edition, Cengage Learning, Stamford CT, 2010, ISBN 0 495 43853 7, pp. 1133-1151.

O'Flaherty, C.A., "Highways: The Location Design, Construction and Maintenance of Road Pavements, 4th Edition", Elsevier, Woburn MA, 2002,ISBN 0 7506 5090 7, especially pp. 34-52.

Sugumaran, Ramanathan et al,"Transportation Infrastructure Extraction" In: Remote Sensing of Impervious Surfaces edited by Qihau Weng, CRC Press, Boca Raton, FL, 2008, ISBN 1 4200 4374 9 especially p. 175.

Sperring, D.G. "A Review of the Effects of Natural Damage" In Cost Effective Maintenance of Railway Track Edited by R. A. Vickers, Institution of Civil Engineers, 2002, ISBN 0 7277 1930 0, pp. 105-116.

Transportation Research Board of the National Academies, "Automated Sensing for Construction Quality Monitoring of Concrete Pavements, and Smart Long-Term Tagging System", Transportation Research Board (TRB) Research Needs Statement, [online] 2013, [retrieved on approximately Dec. 31, 2013] retrieved from the Internet <URL: rns.trb.org/dproject.asp?n=33481>.

Transit New Zealand, "Standard Test Procedure for Benkelman Beam Deflection Measurements", Transit New Zealand Publication T/1, Jun. 1977.

Portas, S et al,"Field Testing and Modelling of the Italian Smart Runway Instrumentations",2010 FAA Worldwide Technology Transfer Conference, Federal Avionics Administration, Atlantic City New Jersey, Apr. 2010.

Yang, S. et al, "Smart Airport Pavement Instrumentation and Health Monitoring", 2014 FAA Worldwide Technology Transfer Conference, Federal Avionics Administration, Galloway, New Jersey, Apr. 2014.

* cited by examiner

EARLY WARNING SYSTEM FOR ROAD, RUNWAY, AND RAILWAY FAILURES

TECHNICAL FIELD

This disclosure relates generally to electronic monitoring and detection, and more specifically to the monitoring and detection of subsurface failures beneath constructions supported by the earth, such as roads.

BACKGROUND

Roads and highways form a major part of any nation's infrastructure, and a major part of any nation's budget. They are used every day by almost everyone, and are the backbone of transportation of commercial goods. Airport runways, likewise, are crucial to a nation's economy. Roads, highways, airport runways, ground-level railway tracks, and river or ocean dikes are referred to collectively as "roads" herein.

The structure of modern roads has evolved gradually since the 17th century into a complex set of layers, whose details vary depending on the materials available, the environment, and the intended use. Well-known engineering principles provide a high level of confidence for the properties and stability of these structures.

However, all such constructions share a common weakness: they are not built with a rigid, self-supporting structure but depend for their support on the underlying ground. Despite the most careful design and planning and the most exacting preparation, the ground behavior after the road has been completed is subject to forces and events which are known statistically but are unpredictable in detail. In particular, cavities and fractures in the underlying strata beneath the road can develop due to floods, gradual erosion, and other geological and hydrologic forces. Leaks of fluids and foreign substances from landfills and hazardous waste dumps can also cause problems.

These cavities reduce the road support leading to pavement distress and possibly catastrophic failure. For a runway, failure consisting only of a slight subsidence could cause an aircraft to lose control on landing. On a highway, the more frequent type of failure is collapse of the pavement into the cavity or, if the road is alongside a precipice, collapse of the road down the precipice.

Subsidence of a railway track, which may not appear until it is put under load, can cause a train to come off the track potentially causing great damage (as discussed in SPERRING, D. G. 'A Review of the Effects of Natural Damage' In: Cost Effective Maintenance of Railway Track, Edited by R. A. Vickers., Institution of Civil Engineers, 2002, ISBN 0 7277 1930 0, pages 105-116.), while a loss of strength in a dike can cause the dike to fail during a severe storm leading to property damage and possible loss of life.

The minimum implication of such a failure is a need for an expensive emergency repair, quite possibly during inclement weather since storms are a common cause of cavitation. In some cases, the collapse may cause the road to be closed for an extended period requiring travel and shipping to be rerouted for days or even months. In extreme cases such as following severe storms, towns can become isolated due to one or multiple failures. In addition, property damage and even loss of life due to vehicles falling into the hole may occur.

Distress surveys are periodically made on important roads to detect pavement distress. However, vulnerability due to subbase or other subsurface materials degradation is not related to visible pavement distress. There do not appear to be any good means currently available for real-time monitoring of roads to discover such subsurface failures.

Geophysical survey methods are sometimes used to evaluate geological conditions during design of the road. O'FLAHERTY, C. A., Highways: The Location Design, Construction and Maintenance of Road Pavements, 4th Edition", Elsevier, Woburn Mass., 2002, ISBN 0 7506 5090 7, especially pages 34-52 comments that "the usefulness of geophysical methods of site investigation for road works has not been demonstrated except in limited applications" and "the proper implementation and interpretation of a geophysical survey requires the use of specialist personnel".

One category of methods for determining subsurface conditions depends on physical manipulation of the region to be tested, either by boring temporary holes or by installing various instrumentation in the road.

One such geophysical survey method is seismic refraction. As described by DALEY, MARGARET A. et al, Seismic Refraction Data Collected in the Chugach Mountains and along the Glenn Highway in southern Alaska in 1984, United States Department of the Interior Geological Survey Open-File Report 85-531 [online], 1985, pages 1 and 3, [retrieved on approximately 2013-12-31] Retrieved from the Internet <URL: pubs.er.usgs.gov/publication/ofr8553>, the use of seismic refraction techniques requires, at each location to be tested, a bore hole of several inches diameter filled with explosives. Approximately five locations per day were tested. U.S. Pat. No. 8,472,674 by Yevskyy describes this technique.

2D resistivity imaging has also been used, especially for looking at possible collapsed mine shafts, and for karst regions. It works on the principle that ground resistance changes when encountering a cavity. However, the nature of the change depends strongly on whether the cavity is water filled. Also, this technique is only applicable in some soil types.

U.S. Pat. No. 5,298,987 by Tomita describes a method using a small hole bored in the pavement for direct visual observation. A separate operation is required for each point to be tested.

U.S. Pat. No. 6,597,992 by Rooney deploys a sensing tool at selected positions. Again, a separate operation is required for each point to be tested but this method also requires that the subsurface material have a known, specific characteristic reference profile.

U.S. Pat. No. 7,788,049 by Bryant uses a plurality of electrodes inserted into the soil connected by communications and power cables. It is possible that the electrodes might remain permanently in place, but during use they are connected to power and measuring equipment which must be manually placed. In U.S. Pat. Application No. 20080042653, Bryant adds a provision for wireless communication and GPS, but the requirement for power still suggests that this equipment is set up and/or used at a single specific location.

U.S. Pat. Application No. 20110161008 by Lee measures land settlement by using magnetic field detection equipment which is adjacent to a hole which is perforated down to an unmovable layer. Again, a separate operation is required for each point to be tested.

Measurement of flexible (typically asphalt, as opposed to rigid concrete) pavement structure is done by subjecting the pavement at suspect locations to stress by using a Benkelman beam, Dynaflect and similar falling weight deflectometers, to measure road deflections according to GARBER, NICHOLAS J. and HOEL, LESTER A., Traffic and Highway Engineering, 4th Edition, Cengage Learning, Stamford Conn., 2010, ISBN 0 495 43853 7, pages 1133-1151. Although these methods can detect weaknesses, they are sufficiently time consuming and equipment-intensive that it is difficult to justify using them routinely. For example, the Benkelman beam requires that at each point to be tested, a hole is drilled in the pavement for temperature measurement. The test appears to require overall as much as an hour per location according to TRANSIT NEW ZEALAND, Standard Test Procedure For Benkelman Beam Deflection Measurements", Transit New Zealand Publication T/1, June 1977. ASTM, Prediction of Flexible Pavement Layer Moduli from Dynaflect and FWD Deflections, American Society for Testing and Materials (ASTM) Report STP1026 [online], January 1989 [retrieved on approximately 2013-12-31] Retrieved from the Internet <URL: www.astm.org/DIGITAL_LIBRARY/STP/PAGES/STP19811S.htm> reports that although the Dynaflect prediction equations were reasonably accurate on the basis of the analytical evaluation, they were considered too complex for practical use.

All of these methods require manipulation of the ground or road at the location to be tested, which limits testing to a small number of locations per day. Thus, geophysical survey methods are probably not useful for routine monitoring of an entire road.

Another category of methods uses equipment which does not require physical modifications to the road. The most popular of these is ground penetrating radar (GPR) technology.

The U.S. DEPARTMENT OF TRANSPORTATION FHA, Ground-Penetrating Radar, Federal Highway Administration (FHA), [online] undated report FHWA-HRT-04-072, HRTS-03/01-04(1M)E [retrieved on approximately 2013-12-31] Retrieved from the Internet <URL: www.fhwa.dot.gov/pavement/groundpr.pdf> says that by using GPR, highway engineers can assess subsurface conditions at a fraction of the cost of conventional methods, claiming that GPR systems can survey pavements quickly and with minimal traffic disruption and safety risks.

However, CARDIMONA, S. at al, Ground Penetrating Radar Survey of Interstate 70 Across Missouri, The University of Missouri-Rolla, Department of Geology and Geophysics and The Missouri Department of Transportation [online], pages 5, 6, and especially 7 [retrieved on approximately 2013-12-31] Retrieved from the Internet <URL: transportation.mstedu/media/research/transportation/documents/i70.pdf> found numerous difficulties in interpreting the recorded data when applying the GPR technology to a stretch of real highway in Missouri. Ground penetrating radar produces a recording of patterns of dielectric constant changes beneath the measuring device. Interpreting this information requires both a pre-existing knowledge of the dielectric constants of all materials (both pavement and soil) which will be encountered during the survey, and also assumes that the road itself is of consistent and continuous structure.

U.S. Pat. No. 5,287,740 by Tomita notes that the GPR measurements are not able to examine the full width of the road or road lane, so that secondary examination is required at suspected locations.

U.S. Pat. Application No. 20030012411 by Sjostrom describes a portable system to detect underground utilities using GPR, including a system for processing and presenting the information.

U.S. Pat. Applications No. 20130018585 and 20130173163 by Zhdanov describe systems for real-time imaging of geological or man-made objects using various geophysical fields. This is a very broad pair of patent applications since they seem to encompass any sort of sensor used with any sort of field, in any configuration. However, they do not actually provide information about how to construct such a system. They seem to be more concerned with methods for combining the results of various methodologies.

Attempts to use remote sensing for assessing road condition have not yet been effective even at discovering pavement surface conditions. SUGUMARAN, RAMANATHAN et al, 'Transportation Infrastructure Extraction' In: Remote Sensing of Impervious Surfaces edited by Qihau Weng, CRC Press, Boca Raton, Fla., 2008, ISBN 1 4200 4374 9 especially page 175 reported that much higher resolution data than is currently available is needed to extract road surface conditions.

Lidar, which uses laser pulses to accurately measure elevation, is a possible approach to remote sensing of road conditions. It is true that lidar can detect pavement subsidences too small to be seen by the unaided eye. However, lidar is a difficult and expensive technology and, except for airport runways, the presence or absence of subsidence is not a strong indicator of subsurface problems.

A final problem which besets all of the techniques described above is that they are ultimately looking for anomalies in the road structure and the underlying geology, rather than looking for actual early-stage damage. They cannot in themselves distinguish between benign and threatening situations.

In general, subsurface changes by their nature cannot be seen visually. BONNET, CLIFFORD F., Practical Railway Engineering, 2nd Edition, Imperial College Press, London, England, 2005. ISBN 1 86094 515 5, especially page 86 mentions that railway track staff are instructed to watch for external signs of slip, such as distorted or leaning signal posts, but these signs can at best detect changes in an embankment, not in the subbase or subgrade.

Thus there is a need for a method and apparatus that can quickly determine the integrity of the material which supports a road, as indicated by Transportation Research Board of the National Academie, Automated Sensing for Construction Quality Monitoring of Concrete Pavements, and Smart Long-Term Tagging System, Transportation Research Board (TRB) Research Needs Statement, [online] 2013, [retrieved on approximately 2013-12-31] retrieved from the Internet <URL: rns.trb.org/dproject.asp?n=33481>.

SUMMARY

Disclosed herein is a method and apparatus for detecting faults beneath a construction supported by earth. The method comprises detecting the conditions of fabric built into the construction supported by earth. One condition of the fabric indicates a fault while a second condition indicates no fault. The detected condition is associated with the location of the fabric that was built into the construction. The detected condition of the fabric is reported. Also disclosed is a fabric that can be included when constructing a road. The fabric is an array of electronic circuits, arranged such that stretching or tearing the fabric will damage electrical characteristics of the fabric. An apparatus for detecting faults beneath a road is also disclosed. The apparatus comprises a fabric built into the road, and a sensor apparatus configured to measure conditions of the fabric at multiple locations. A subset of the conditions of the fabric indicates faults beneath the road.

Deterioration of the subsurface structure of a road can lead to unanticipated collapse of said road, which in turn incurs the expense of emergency repairs, economic losses due to traffic rerouting, possible destruction of property, injury to people or animals, or even death.

The systems and methods disclosed herein make it possible to monitor the condition of a road, so that the existence and extent of possible collapse can be discovered and planned for. Thus, an agency responsible for the road can avoid extra costs associated with emergencies, traffic rerouting can be planned for convenient times to reduce the economic impact, and damage to property and individuals can be averted.

DETAILED DESCRIPTION

Figure 1:
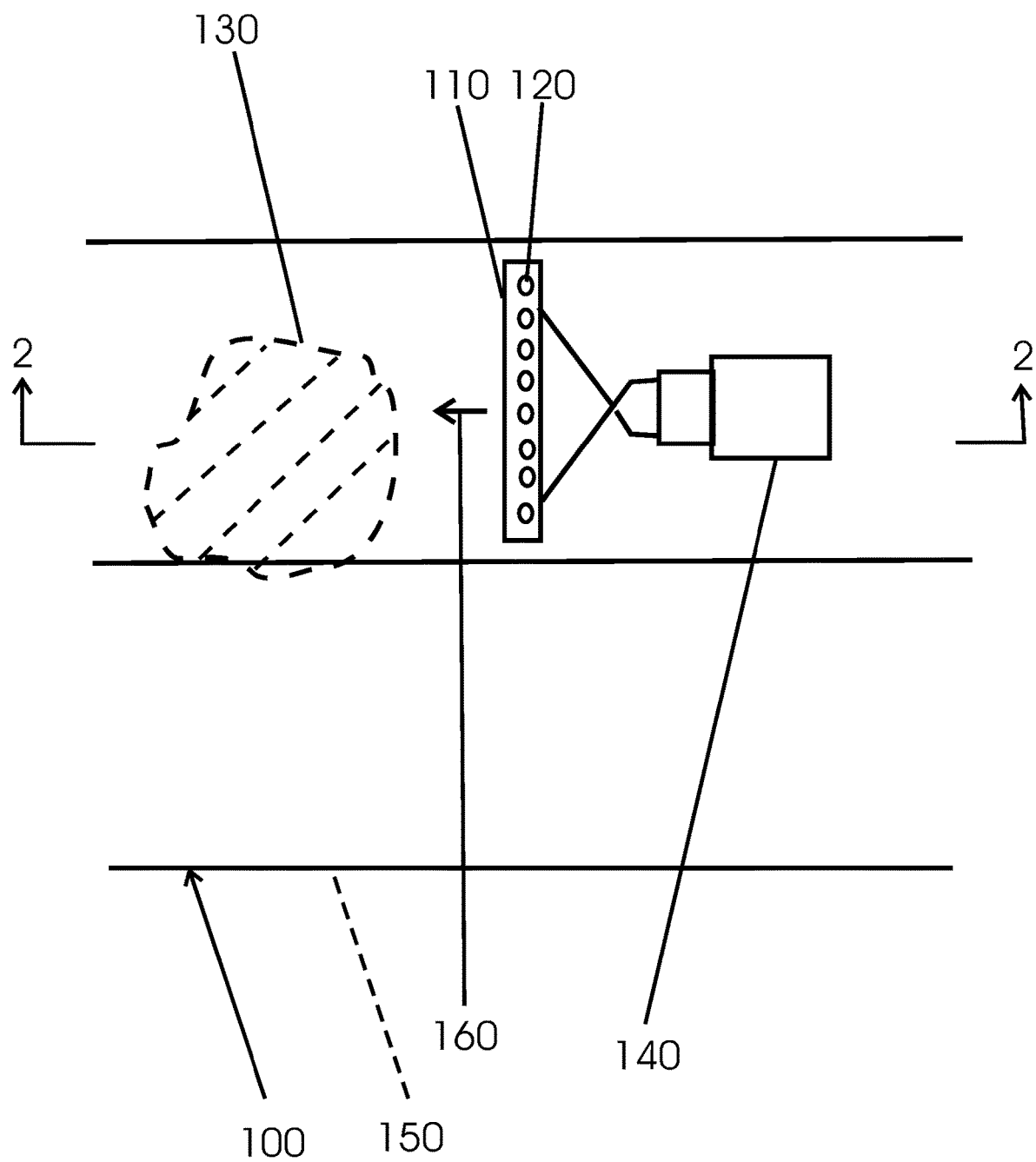
FIG. 1 is a top view diagram of a method and apparatus for detecting incipient road failure.

Disclosed herein is a method and apparatus for real-time monitoring and detection of subsurface failures of a road, highway, airport runway, railway track, river or ocean dike, or similar construction which is earth supported. Both the method and apparatus can detect faults beneath a road or similar construction which can cause collapse. An intelligent fabric is built into such a road, either inside or between pavement layers, when said road is constructed or rebuilt. As seen in FIG. 1, in some implementations a sensor assembly 110 may be conveyed 160 along a road 100 by a vehicle 140 to detect cavities or other subsurface weaknesses 130 anywhere within the road or some lanes of said road. When said sensor assembly activates said fabric remotely, damage to said fabric, and thus to said road, can be detected. The possible damage can be shown as an image, activate an alarm, be stored for future examination, or any combination of these actions.

The following definitions are used herein:

The word "road" should be understood to include any paved or non-paved way which is earth-supported, including roads, highways, airport runways, ground-surface railway tracks, and dikes.

The word "pavement" includes all of the layers of the road construction, from the surfacing course down to the subbase.

The word "fabric" refers to a material in the general form of a sheet or mesh, which has a predetermined width which is a major fraction of the width of a road or one lane of a road, and a length typically larger than several car lengths.

The phrase "intelligent fabric" refers to a fabric which includes means for determining and reporting its own physical condition.

The phrase "regular array" refers to a repeated pattern used in forming a fabric, such that all regions of the fabric have approximately the same geometric pattern.

The word "sensor" refers to a to a device for detecting or measuring some physical phenomenon.

The phrase "sensor assembly" refers to an assemblage of one or more sensors of a specific type, together with electronics and computing capabilities suitable for gathering data from the sensors and processing it into a useful form.

The verb "monitor" refers to the process of observing, measuring, or examining an object or phenomenon, either continuously or periodically.

The phrase "RFID sensor" refers to an electronic device which can send a radio frequency query to an RFID tag, and can receive the response if any.

The phrase "RFID tag" refers to a non-powered electronic device capable of detecting and responding to a radio-frequency inquiry from an RFID sensor. RFID tags are very small, very inexpensive microelectronic components with an ability to detect and respond to an electronic (radio) query. Power for an RFID tag response comes from said query, so an RFID tag does not need any additional power source.

A very common use for RFID tags and sensors is in a retail store's theft management system, where an RFID tag embedded in the merchandise can respond when queried by electronic gates at a store exit. If a customer has properly paid for merchandise, a store clerk will have disabled said RFID tag and said customer will be allowed to leave.

The word "loop" refers to an electrical circuit comprising several wire segments connected to form a resonant circuit which is resonant at a specified frequency. Said resonant frequency does not depend on the exact shape of the loop (square, hexagonal, etc) but only on the total perimeter.

The phrase "loop sensor" refers to an electronic device which can detect whether it is close to a loop of a specified resonant frequency.

The phrase "location sensor" refers to a means for reporting the current time and location. Said means can be a global positioning system (GPS), or measurement devices known as inertial systems which discover location by monitoring vehicle travel time and direction.

The phrase "line buffer" refers to a computer memory element which accumulates data which constitutes one line of image data.

The early warning system disclosed herein provides a method and apparatus for real-time monitoring and detection of subsurface failures of a road, highway, airport runway, railway track, river or ocean dike, or similar construction which is earth supported. The system allows the presence or absence of potentially dangerous faults beneath the road to be quickly and easily discovered.

Some implementations of the system comprise a material or fabric which must be built into a road, either inside or between pavement layers or above the subgrade, when said road is constructed or rebuilt, plus a sensor assembly. The fabric may be embedded within the pavement of the road. There is no requirement for physical access to said fabric after road construction and said fabric is entirely passive except during examination. In some implementations, the fabric is included in the construction of a road to permit detecting potential failures in the road in such a way that stretching or tearing the fabric will cause damage to its electrical characteristics. The fabric comprises a regular array of electronic circuits or devices, from which the potential for road failure can be inferred. An examination permits discovery of damage to the subsurface structure of a road, before damage becomes apparent on the surface through subsidence or collapse.

Examining the condition of a road is done by passing a suitable sensor assembly along the surface of said road, for example by attaching said sensor assembly to a car or truck. In some implementations, a sensor assembly examines the condition of a road by detecting the physical integrity of an embedded fabric. In some implementations, the sensor assembly comprises a linear sensor array of a predetermined number of radio frequency transmitter and receiver pairs which form sensors whose characteristics match the electrical characteristics of the embedded fabric. The sensor assembly can include a vehicle or other means to move the linear sensor array along the road, such that the array of sensors is deployed across the road while the vehicle is moving along the road. The sensor assembly may also include signal processing hardware and software which collects and accumulates data from the array of radio frequency devices, so that defects in or beneath said road can be discovered. When the sensor assembly activates the fabric remotely, damage to the fabric, such as a tear, becomes apparent. This damage is assumed to imply possible damage to road structure, and can be shown as an image or automatically processed using conventional image-processing techniques. The sensor assembly is constructed to detect potential failures across the full width of a road or road lane.

FIG. 1 shows a top view of a method and apparatus to monitor the subsurface condition of a road 100, which in some implementations may be highway, airport runway, or similar construction which is earth supported. Said road includes a fabric 150 (not visible in FIG. 1) which can determine and report its own physical condition. A sensor assembly 110 for examining a condition of a road by detecting the physical integrity of an embedded fabric is conveyed 160 along said road by a vehicle 140 to detect cavities or other subsurface weaknesses 130 which develop over time. The sensor assembly includes a predetermined number of sensors 120 arranged transversely to the direction of motion of said sensor assembly. In some instantiations, the sensor assembly comprises a linear sensor array of a predetermined number of radio frequency transmitter and receiver pairs which form sensors whose characteristics match the electrical characteristics of the embedded fabric. In some instantiations, other means than a vehicle may be used to move 160 the array along the road, such that the array of sensors is deployed across the road while the array is being moved 160 along the road. The sensor assembly may also include signal processing hardware and software which collects and accumulates data from the array of radio frequency devices. Thus, defects in or beneath the road can be discovered. In some implementations, when the sensor array apparatus, including the signal processing hardware and software, is mounted in or on a vehicle, an operator of the vehicle may be immediately alerted to road problems.

Figure 2:
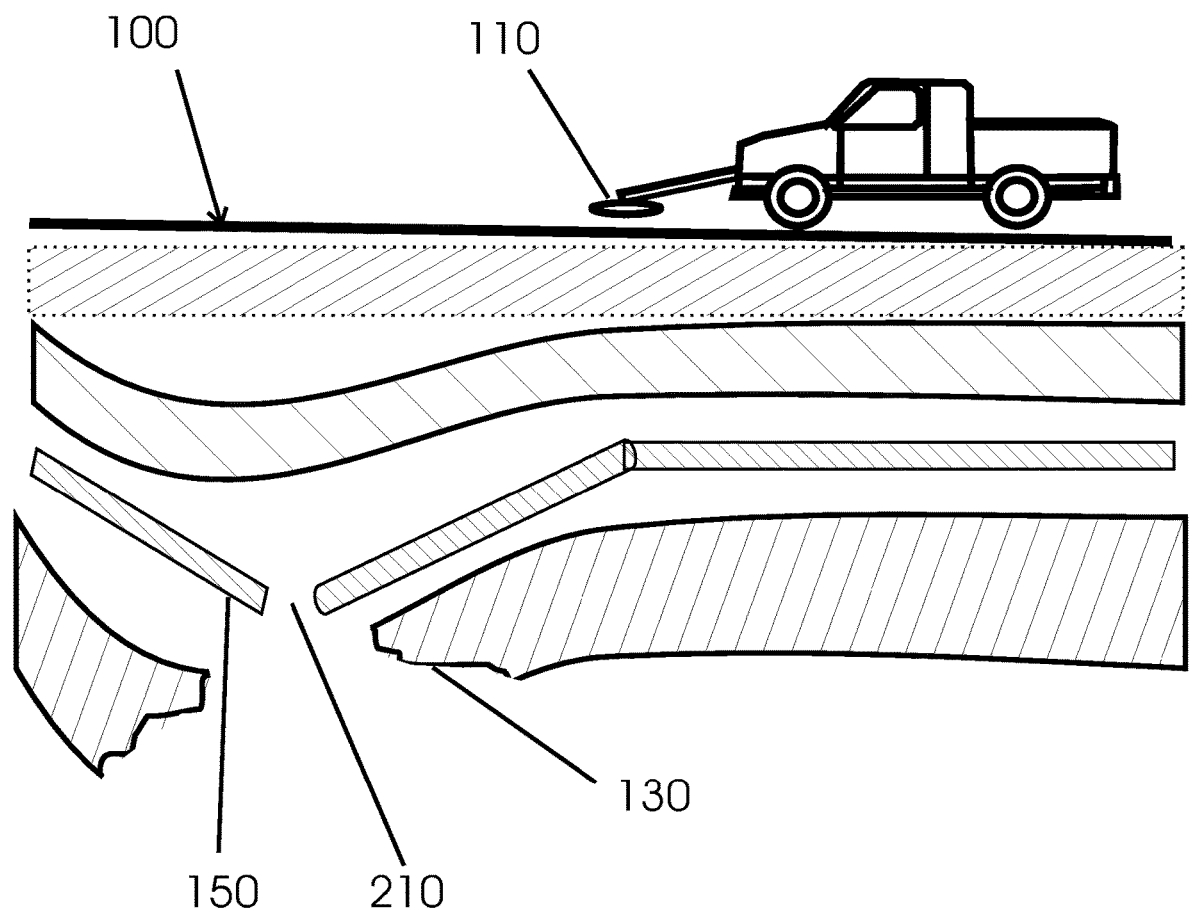
FIG. 2 is a side view diagram of the instantiation shown in FIG. 1.

FIG. 2 shows a side view of the method and apparatus shown in FIG. 1 along section line 2-2. A fabric 150 is built into the road 100 foundation during road construction or rebuilding. When a subsurface weakness or cavity 130 develops, said fabric tears 210 or is otherwise damaged. This damage or tear in the fabric 210 can be detected easily and inexpensively using the above-road sensor assembly 110.

Figure 3:
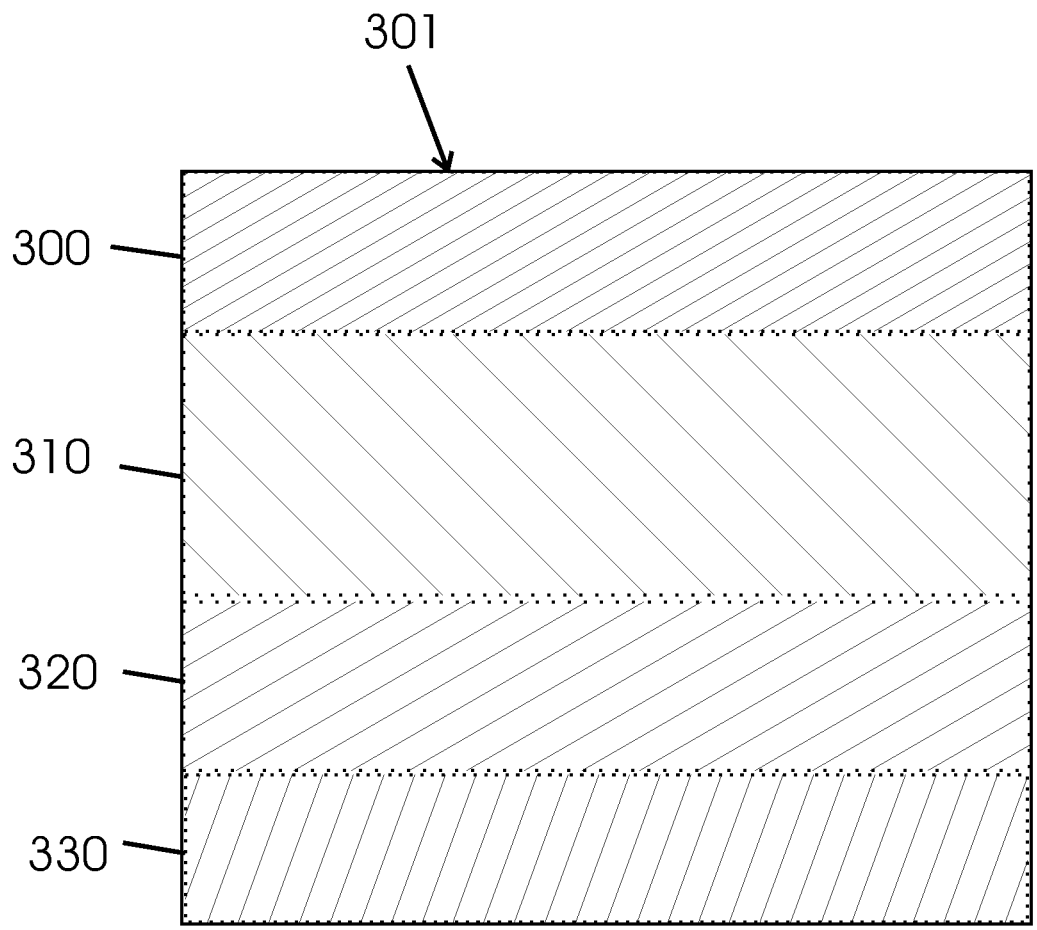
FIG. 3 shows a cross-section of a prior art structure of a road with flexible pavement.

FIG. 3 shows a cross section of a typical road 301 built with a flexible pavement according to modern design. Such a road will have a variable number of layers and sublayers, depending on the purpose and geographic location of the road. The surfacing may include a base course 300 and a wearing course 310. Both the roadbase 320 and the subbase 330 may comprise one or several sublayers. Finally, the subgrade is the earth which supports the road. A road with rigid pavement will be approximately the same except that the surfacing is replaced by a concrete slab.

Figure 4:
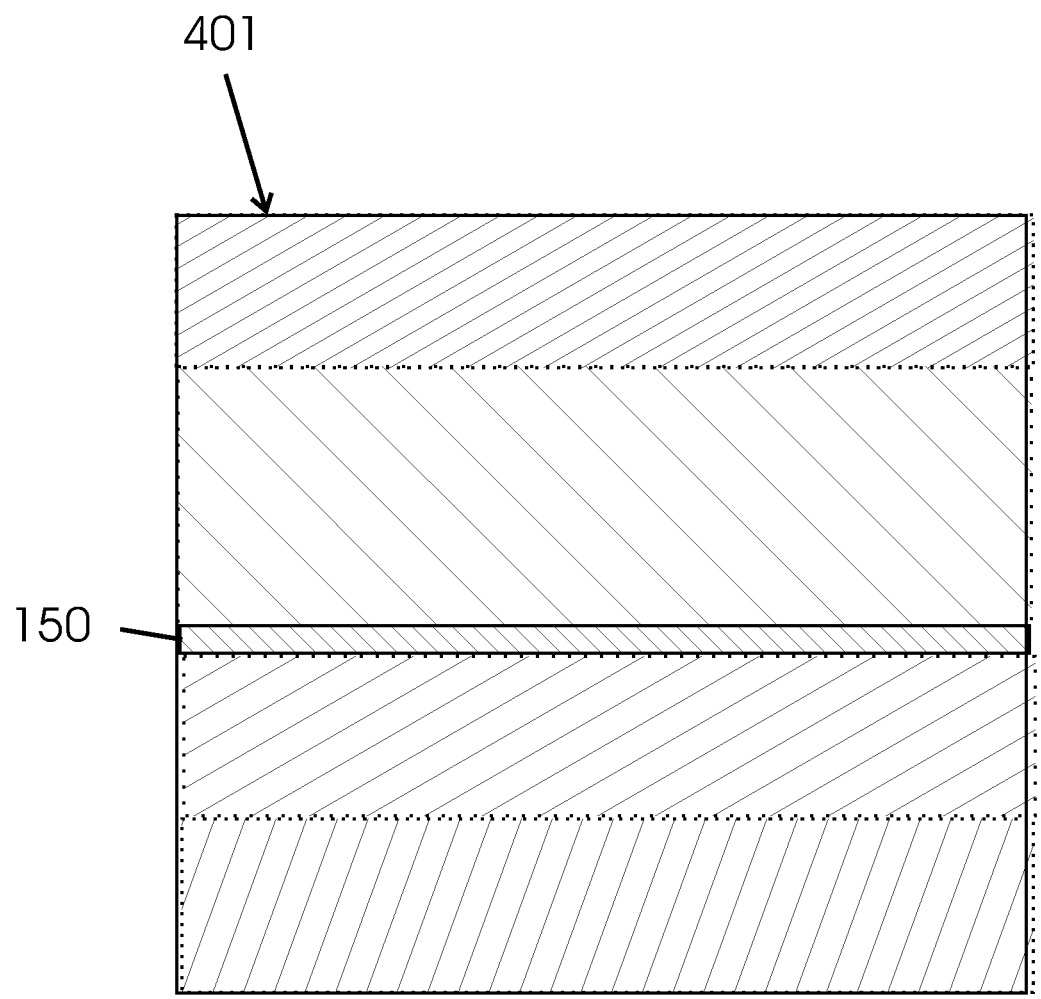
FIG. 4 shows a typical structure of a road with flexible pavement, with the fabric disclosed herein incorporated in the structure according to one instantiation.

FIG. 4 shows a cross section of road 401, similar to road 301, but with the fabric 150 added. The fabric 150 comprises a regular array of electronic circuits or devices, from which potential for road failure can be inferred. In some instantiations, the fabric may comprise a regular array of a plurality of microelectronic devices which can respond to a radio-frequency signal, such that damage to the fabric also damages one or more of the microelectronic devices to an extent that the device can no longer respond to the radio-frequency signal. Thus, damage to the fabric can be detected and potential for road failure can be inferred therefrom.

Figure 5:
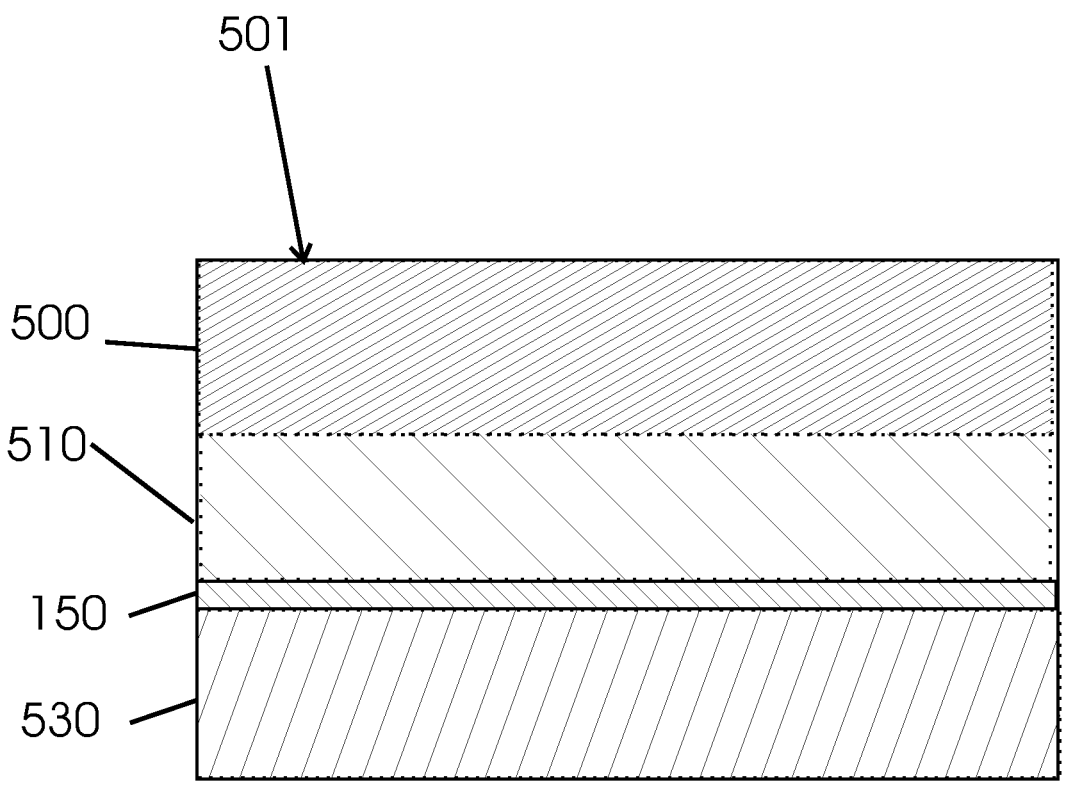
FIG. 5 shows a typical structure of a road with concrete pavement, with the fabric disclosed herein incorporated in the structure according to another instantiation.

FIG. 5 shows a cross section of a road 501 with rigid pavement comprising a concrete slab 500, one or more road courses 510, subbase 530, and fabric 150. The subbase 530 may comprise one or several sublayers. The fabric 150 comprises a regular array of electronic circuits or devices, from which potential for road failure can be inferred. In some instantiations, the fabric may comprise a regular array of a plurality of interconnected wires which can respond to a radio-frequency signal at a frequency which matches the prespecified resonant frequency of the array of wires, such that damage to the fabric also breaks one or more of the wires or wire segments thereby changing the resonant frequency of the damaged region of said fabric which includes the broken wire or wire segment. Thus, damage to the fabric 150 can be detected and potential for road failure can be inferred therefrom.

Figure 6:
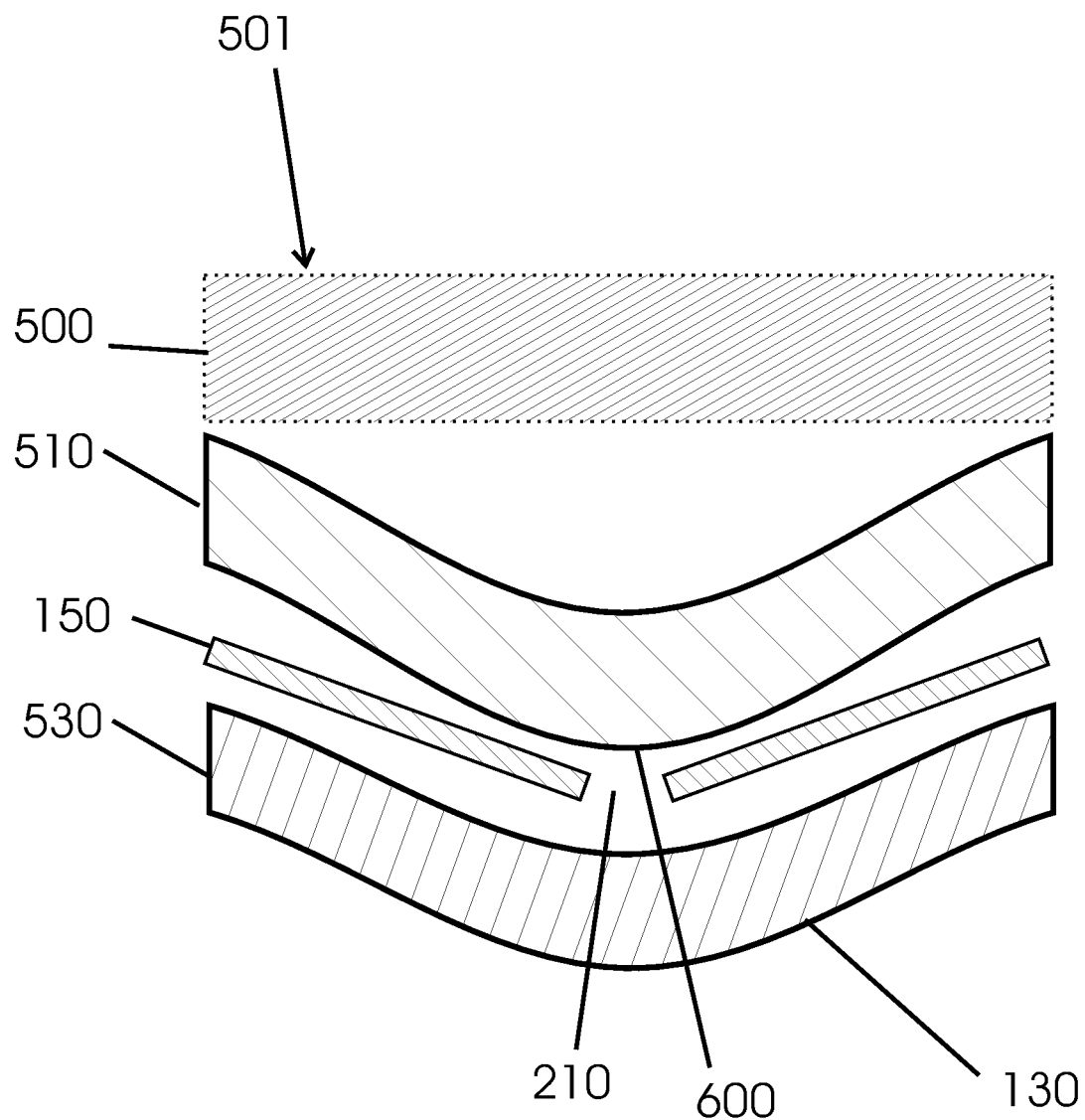
FIG. 6 shows a typical situation in which the fabric disclosed herein is being used to image a defect in a road.

FIG. 6 shows a cross section of a road 501, under which a cavity 130 has appeared. Under normal conditions, a fabric 150 built into the road 501 will remain in more-or-less the same condition as when the road was built. However, when the cavity 130, which might be an actual opening or a collapsed abandoned mine shaft or tunnel, or just an unexpected compression of the subgrade appears, the road courses 510, below the concrete slab 500 or other surface layer (not shown) sag 600 towards said cavity. This reduces the support for said concrete slab 500. In the near future, said concrete slab is likely to fail, particularly when subject to a heavy load. The tear or damage 210 to said fabric can be detected easily and inexpensively using the above-road sensor assembly disclosed herein.

Figure 7:
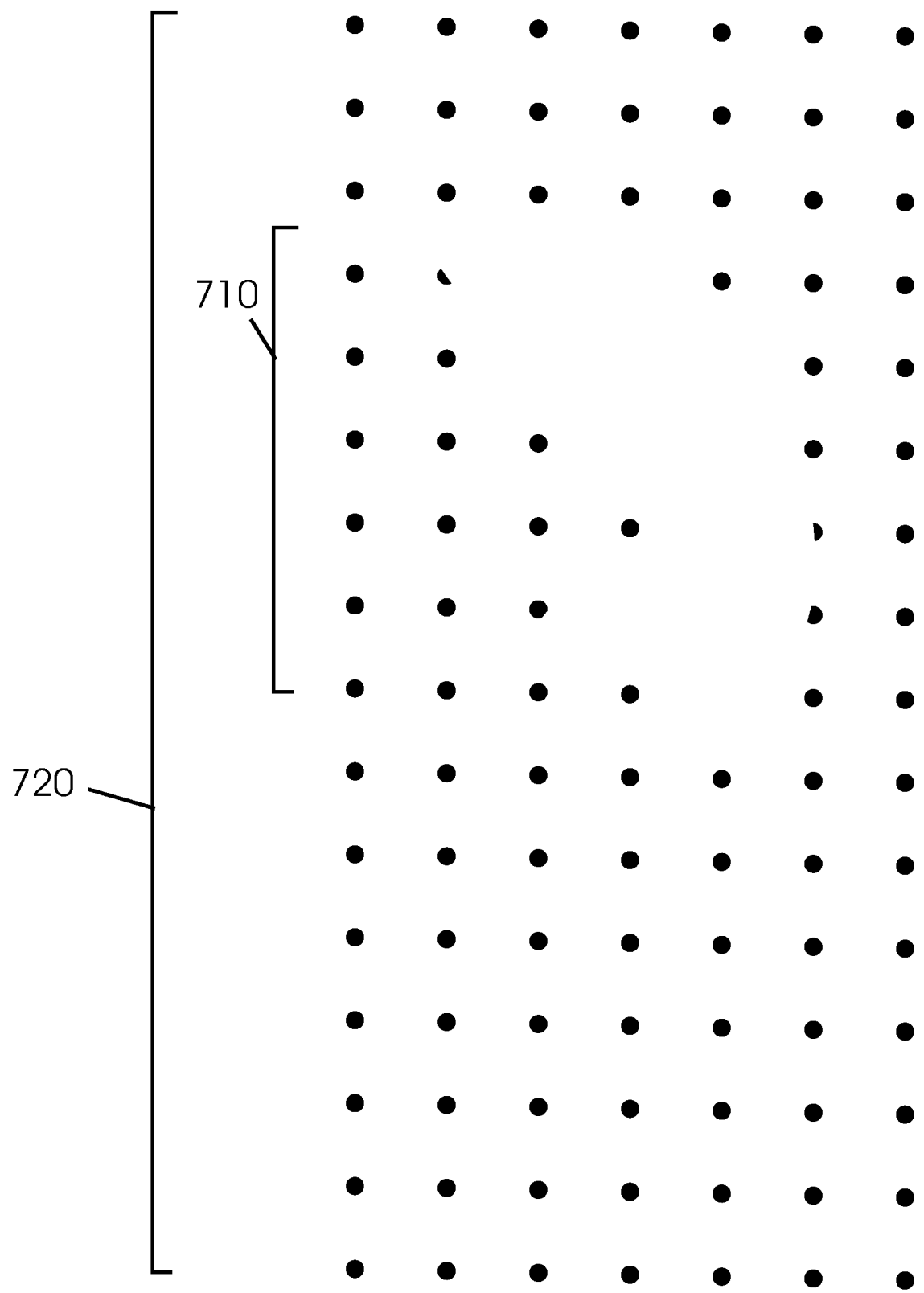
FIG. 7 shows an image of road damage as it might appear on a sensor assembly display as disclosed herein.

FIG. 7 shows an image of a cavity which appears as an irregular gap 710 against an otherwise uniform background pattern 720 on a display. The data being gathered from the sensors in said sensor assembly and shown on said display are processed in ways which are well-known to image processing professionals.

Figure 8:
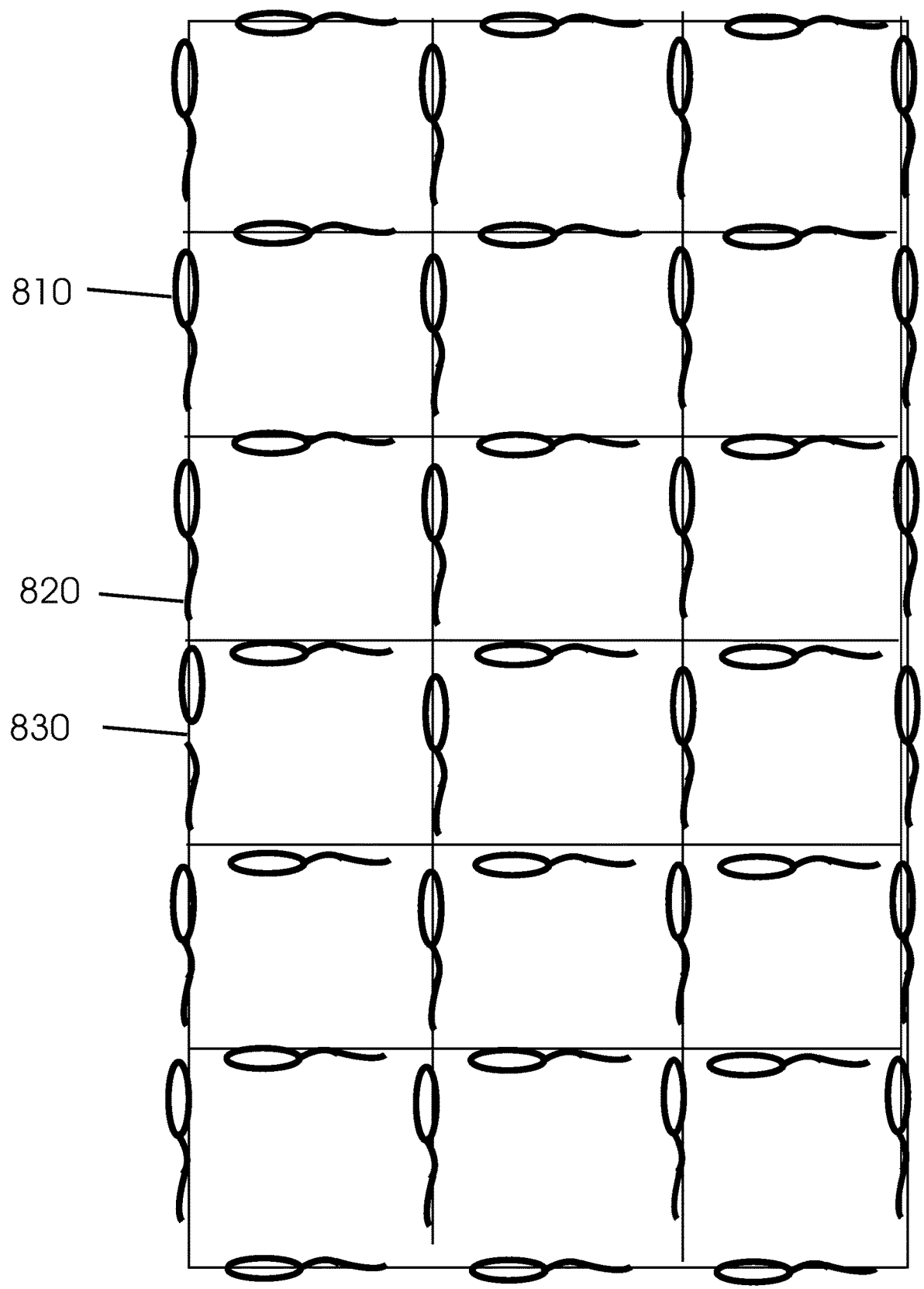
FIG. 8 shows a fabric detail according to an instantiation.

FIG. 8 shows a detail of a fabric which is the first embodiment. RFID tags 810 are arranged in the fabric in such a way that adjacent tags do not touch each other. In other words, adjacent RFID tags are not in electrical contact with each other. Physically, an RFID tag includes a head, where the electronics are, and a tail, or antenna, which is really just a piece of wire or other conductive material to receive and transmit radio waves. Each of the tags has a tail, or antenna 820, which extends along said fabric. Thus, a fabric tear or damage breaks 830 the antennas of some RFID tags and therefore renders some of said RFID tags inoperable.

Figure 9:
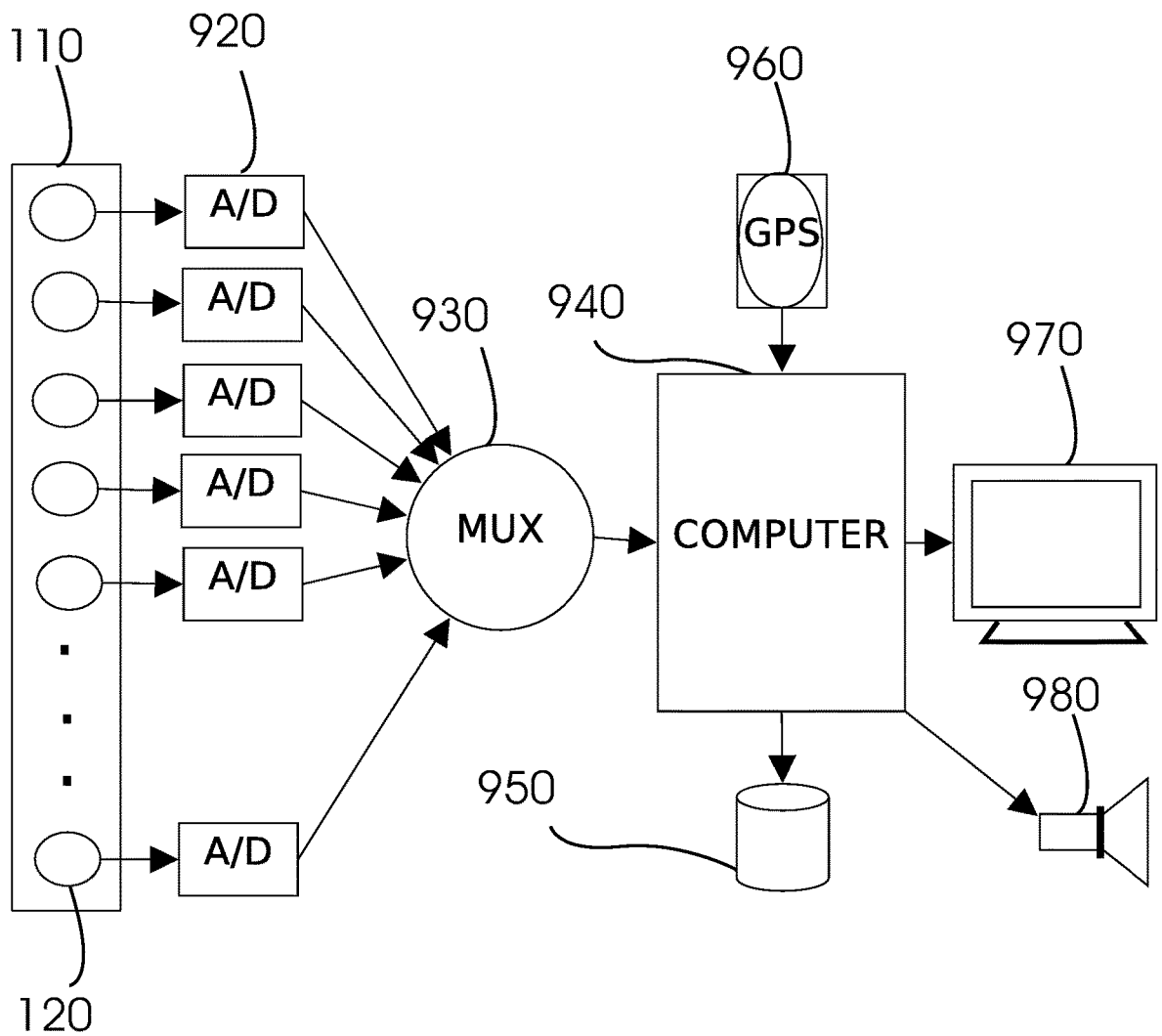
FIG. 9 shows a possible block diagram of a sensor assembly according to an instantiation disclosed herein.

FIG. 9 shows a block diagram for one possible implementation of a sensor assembly to be used with said fabric. An array 110 of sensors 120 produces measurements which are converted to digital form using conventional analog-to-digital converters (A/D, 920), and made available to a multiplexor (MUX, 930). A microprocessor or other computer 940 with associated memory collects said measurements in sequence. The computer 940 may be implemented in a number of different forms. For example, it may be implemented as a cellular telephone. It may also be implemented as part of a smart phone, personal digital assistant, a computer tablet, or other similar mobile device, or a laptop or personal computer (PC), or as an embedded system. One set of measurements constitutes one line of data across a road. Each such line is tagged with exact time and location from a location sensor such as a geographic positioning system receiver (GPS, 960) or the like and saved to a disk file 950 or the like for later processing and/or displayed as one line of an image on a display 970 and/or used to warn the operator of said sensor assembly by triggering an alarm 980 or other indicium.

In some implementations, the sensor assembly for examining the condition of a road by detecting a physical integrity of an embedded fabric, comprises a linear sensor array, a means to move the linear sensor array along the road so that the array of sensors is deployed across the road while being moved along the road, and remotely located signal processing hardware and/or software at some other location, so that more extensive processing or less expensive sensor assemblies may be used. The linear sensor array may be a predetermined number of radio frequency transmitter and receiver pairs which form sensors whose characteristics match the electrical characteristics of the embedded fabric. The means to move the array along the road may be a vehicle or the like. The signal processing hardware and software collects and accumulates data from the array of radio frequency devices. Thus, defects in or beneath the road can be discovered. The sensor array apparatus may include some signal processing hardware and software which are mounted in or on the vehicle or other means of moving the array in addition to the remotely located signal processing hardware and/or software. The operator of the vehicle may be immediately alerted to road problems via the hardware and software mounted in or on the vehicle. In some implementations, the sensor array is mounted in or on the vehicle or other means of moving the array and data is recorded or transmitted to the signal processing hardware and software at some other location, whereby more extensive processing or less expensive sensor assemblies may be used.

Figure 10:
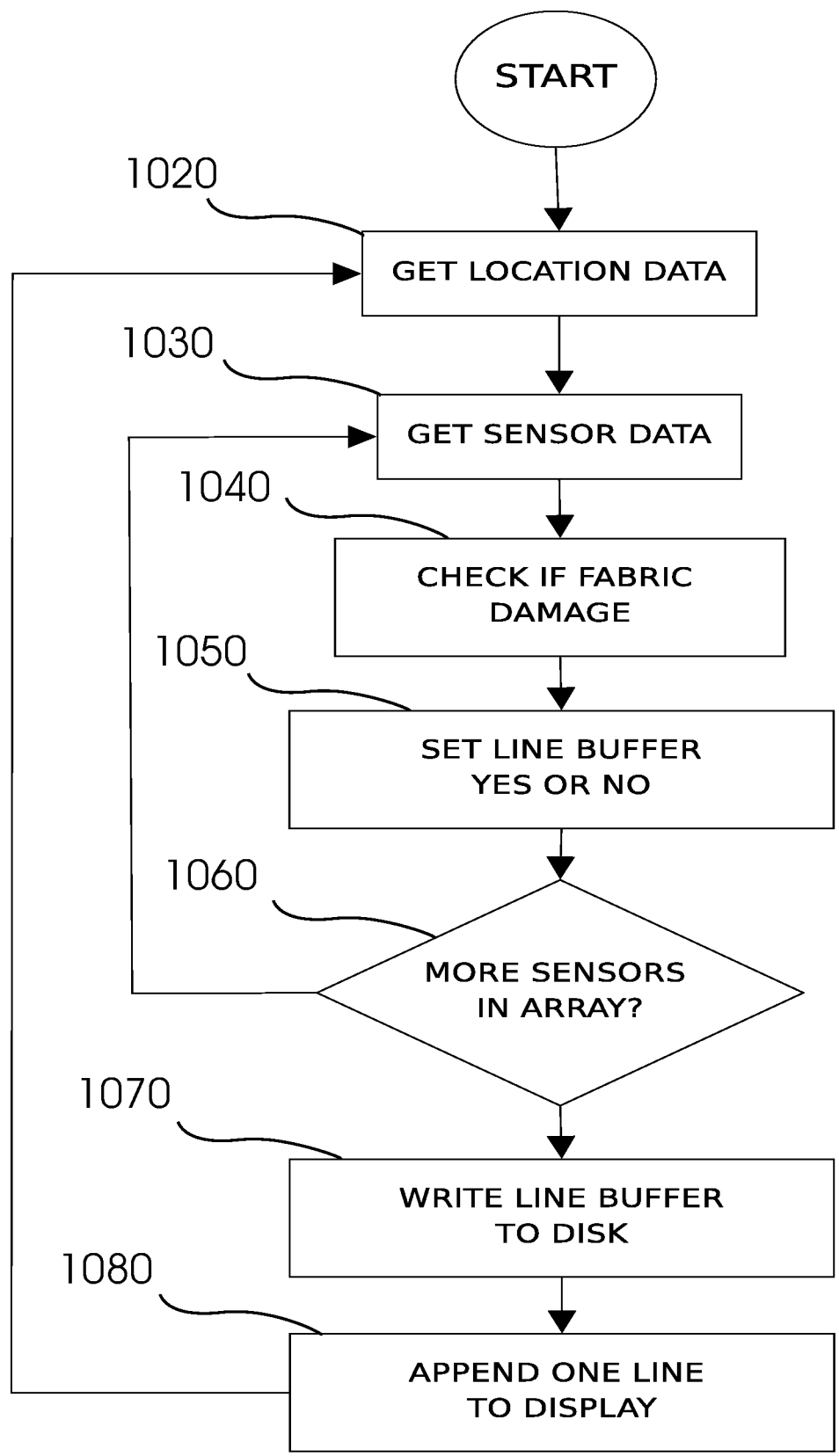
FIG. 10 shows a possible flow chart of software for a sensor assembly according to an instantiation disclosed herein.

FIG. 10 shows a flow chart for one possible implementation of software for a sensor assembly to be used with the fabric disclosed herein. Said software comprises an infinite cycle in which it first gets time and location data 1020. For each sensor in an array which is transverse to the travel direction said software then obtains measured sensor data 1030, checks to see whether said data indicates a damaged fabric 1040, and stores this information in a line buffer 1050 memory. After all sensors in said array have been processed 1060 said software may write said line buffer contents to disk 1070 and/or append said line buffer contents to an on-going display 1080 and/or produce an alert in some other way. All above-listed steps are then repeated.

All of the following items are available off-the-shelf and in customized versions from electronics suppliers, and are not described in detail here: RFID tags, RFID sensors, radio frequency transmitters and receivers, analog-to-digital converters, multiplexors, and microprocessor components and systems. Free and open-source software available for image processing includes OpenCV from Intel® Corporation, and OpenGL from OpenGL.org.

In some implementations, the condition of the lower layers of a road is determined by passing a linear array of RFID sensors along the surface of said road. As said sensors pass over RFID tags embedded in said road, only RFID tags which are not damaged will respond. Thus, as shown in FIG. 7, a matrix 720 of data points is derived which reveals which RFID tags are inoperable.

Figure 11:
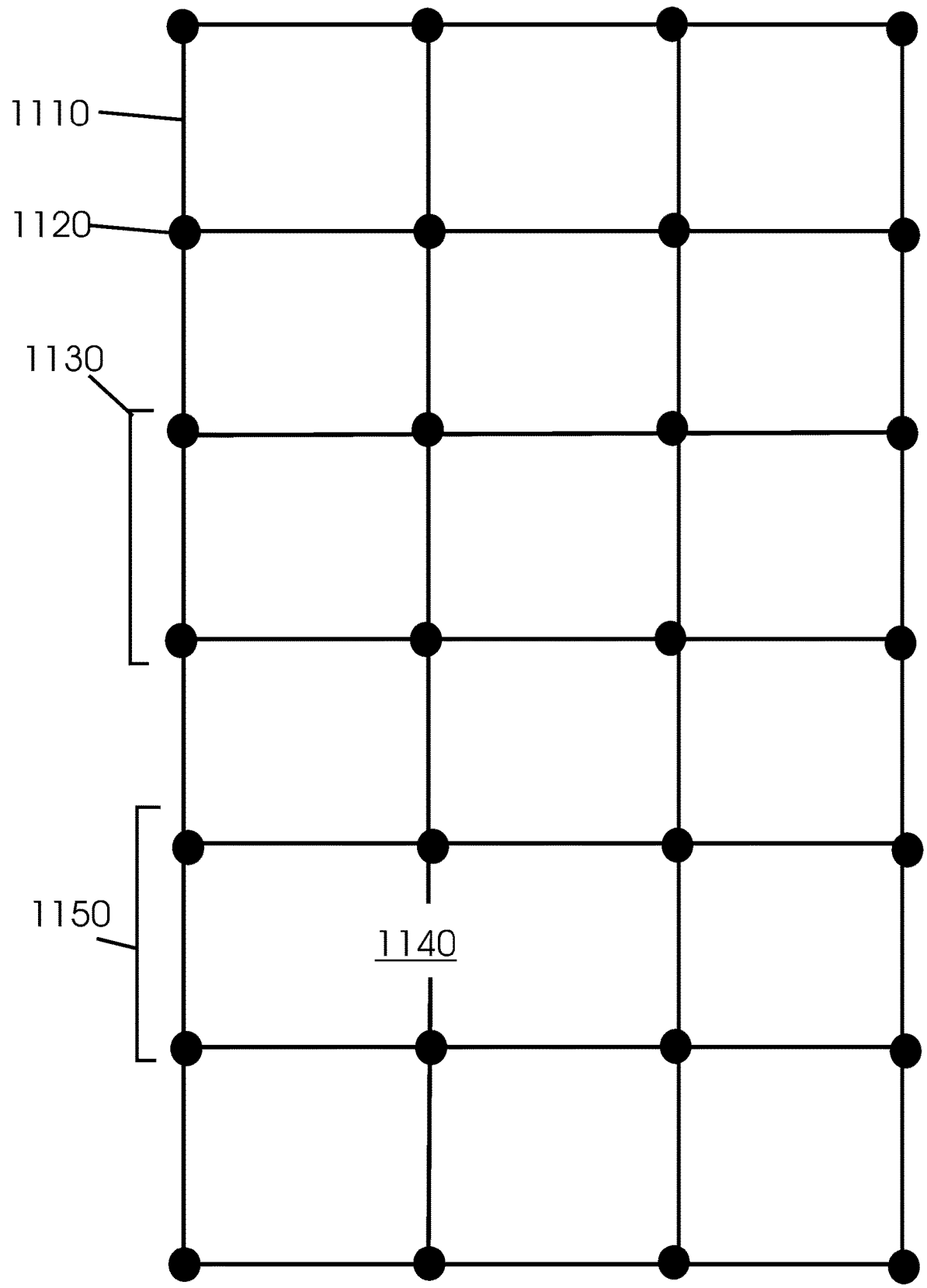
FIG. 11 shows a fabric detail according to another instantiation.

FIG. 11 shows a detail of a fabric which is another embodiment. Wires 1110 which make up said fabric are arranged in a mesh, wherein said wires are electrically connected at each intersection 1120. Each set of wire segments and connections forms a loop 1130 with a specific resonant frequency. When said loops are intact they will resonate and absorb energy at a prespecified intended frequency when a radio frequency transmitter is in operation close to said loop. Said energy absorption can be detected using well-known methods. When one or more wires have been broken 1140 as a result of damage to said fabric, the remaining wires form broken loops 1150 that will no longer resonate and absorb energy at the prespecified intended frequency. This is a principle well known to radio amateurs and others in the field.

In this embodiment, the condition of the lower layers of a road is determined by passing a linear array of radio frequency transmitters along the surface of said road. As said transmitters pass over the loops, only those loops which are not damaged will respond at the prespecified resonant frequency. Thus, as shown in FIG. 7, a matrix 710 of data points is derived which reveals which wires have been broken.

Figure 12:
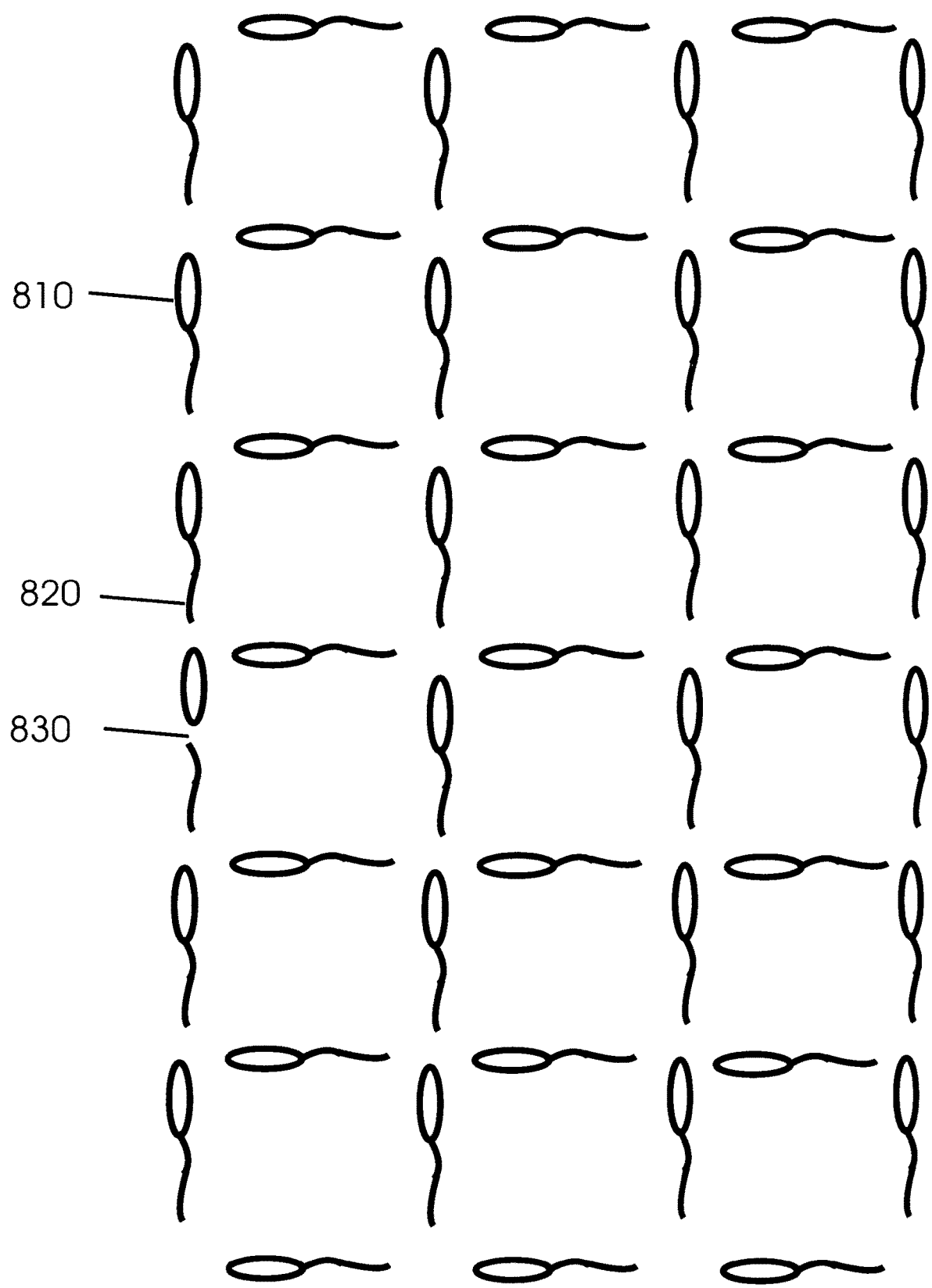
FIG. 12 illustrates a regular array of RFID tags forming a fabric.

FIG. 12 shows a detail of a fabric in another embodiment. RFID tags 810 are arranged in a regular array in the general form of a sheet or mesh thereby forming a fabric as described herein above. Each RFID tag 810 has an antenna 820 which extends towards, but does not touch, the head of an adjacent RFID tag. When an RFID tag is damaged 830 it is rendered inoperable.

The early warning system disclosed herein provides a method and apparatus for real-time monitoring and detection of subsurface failures of a road, highway, airport runway, railway track, river or ocean dike, or similar construction which is earth supported.

Deterioration of subsurface structure of a road can lead to unanticipated collapse of said road, which in turn causes expenses to perform emergency repairs, economic losses due to traffic rerouting, possible destruction of property, injury to people or animals, and even death.

Implementations of the early warning system disclosed herein makes it possible to monitor road conditions so that possible collapse can be discovered and planned for. This is a need which has been identified as high priority by the Transportation Research Board of the National Academies, Automated Sensing for Construction Quality Monitoring of Concrete Pavements, and Smart Long-Term Tagging System, Transportation Research Board (TRB) Research Needs Statement, [online] 2013, [retrieved on approximately Dec. 31, 2013] retrieved from the Internet <URL: rns.trb.org/dproject.asp?n=33481>. Furthermore, it is a capability which is not met by prior art.

Collection, processing, and presentation of sensor array data are well-known in the industry. The arrangements in FIG. 10 and FIG. 11 are only intended to show one way that such processing could be done. Furthermore, although FIG. 7, FIG. 8, and FIG. 11 show square arrays, the arrays need not be square and could be other shapes such as rectangular, triangular, or hexagonal.

Thus, various implementations of the systems and methods described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language.

To provide for interaction with the user, the systems and techniques described here can be implemented on a computer with or without a display device (e.g., a CRT (cathode ray tube) or LCD (liquid crystal display) monitor) for displaying information to the user and with or without a keyboard and a pointing device (e.g., a mouse or a trackball) by which the user can provide input to the computer. Other kinds of devices can be used to provide for interaction with the user as well; for example, feedback provided to the user can be any form of sensory feedback (e.g., visual feedback, auditory feedback, or tactile feedback); and input from the user can be received in any form, including acoustic, speech, or tactile input.

The systems and methods described here can be implemented in a computing system that includes a back end component (e.g., as a data server), or that includes a middleware component (e.g., an application server), or that includes a front end component (e.g., a client computer having a graphical user interface or a Web browser through which the user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, the logic flows depicted in FIG. 10 do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

It will be appreciated that the above implementations that have been described in particular detail are merely examples or possible implementations, and that there are many other combinations, additions, or alternatives that may be included.

Further, systems described herein may be implemented via a combination of hardware and software, as described, or entirely in hardware elements. Also, the particular division of functionality between the various system components described herein is merely example, and not mandatory; functions performed by a single system component may instead be performed by multiple components, and functions performed by multiple components may instead performed by a single component.

Some portions of the above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed implementations may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture. The computer-readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

While the disclosure has been described in terms of various specific implementations, instantiations and embodiments, it will be recognized that the disclosure can be practiced with modification within the spirit and scope of the claims.

The invention claimed is:

1. A method of detecting faults beneath a construction supported by earth, the method comprising:
    detecting, via a sensor assembly, one of a plurality of electrical conditions of a fabric built into the construction supported by earth, the fabric including a plurality of radio frequency identification (RFID) tags, each RFID tag having a head comprising electronics and a tail comprising an antenna configured to break in the event of a fault below the surface of the construction supported by earth, wherein the plurality of electrical conditions of the fabric includes a first electrical condition in which at least one of the antennas is damaged indicating damage to the fabric corresponding to a fault below the surface of the construction supported by earth, wherein said damage to the at least one antenna prevents the at least one RFID tag associated with the at least one damaged antenna from responding to a radio-frequency signal from the sensor assembly and a second electrical condition in which at least one of the plurality of antennas respond to the radio-frequency signal from the sensor assembly, associating the detected electrical condition with a location of the fabric built into the construction, and reporting the detected electrical condition of the fabric at the associated location.

2. The method of claim 1, wherein the detecting comprises sending a radio-frequency inquiry from a sensor in the sensor assembly.

3. The method of claim 1, wherein the detecting comprises passing a radio-frequency transmitter along a surface of the construction.

4. The method of claim 1, wherein the construction supported by earth is a road.

5. The method of claim 4, wherein the fabric is built into the road at a position selected from the group consisting of beneath all layers of the road or between adjacent layers of the road.

6. The method of claim 4, wherein the road includes pavement layers and the fabric is build into the road inside the pavement layers.

7. The method of claim 1 wherein the second electrical condition comprises all of the plurality of antennas within range of the radio frequency signal from the sensor assembly responding to the radio frequency signal.

8. A fabric comprising:
a plurality of radio frequency identification (RFID) tags, each RFID tag having a head comprising electronics and a tail comprising an antenna configured to break in the event of a fault below the fabric, wherein stretching or tearing said fabric will damage at least one antenna of the RFID tags comprising the fabric, and wherein said damage to at least one of the antennas prevents said RFID tag associated with the damaged antenna from responding to a radio-frequency signal.

9. An apparatus for detecting faults beneath a road, comprising:
a fabric built into said road, wherein said fabric includes a plurality of radio frequency identification (RFID) tags, each RFID tag having a head comprising electronics and a tail comprising an antenna configured to break in the event of a fault below the surface of the road; and an above-road sensor apparatus configured to measure electrical conditions indicating physical integrity of said fabric at multiple locations, wherein a subset of the electrical conditions of said fabric indicates faults beneath said road that prevent at least one RFID tag from responding to the above-road sensor apparatus.

10. The apparatus of claim 9, wherein the fabric comprises a regular array of electronic circuits.

11. The apparatus of claim 9, wherein the fabric can respond to a radio-frequency signal from the sensor apparatus.

12. The apparatus of claim 9, wherein the fabric includes a means for determining and reporting the electrical conditions of the fabric at one or more locations.

13. The apparatus of claim 9, wherein the radio frequency identification (RFID) tags are arranged in a mesh and the RFID tags are not interconnected.

14. The apparatus of claim 9, wherein the sensor apparatus is configured to measure electrical conditions of the fabric by being passed along a surface of the road.

15. The apparatus of claim 9, wherein the fabric is located at a position selected from the group consisting of beneath all layers of the road or between adjacent layers of the road.

16. The apparatus of claim 9, wherein the fabric is built into the road.

* * * * *